(12) United States Patent
Formato

(10) Patent No.: US 12,162,978 B2
(45) Date of Patent: Dec. 10, 2024

(54) RADIATION CURABLE PHASE CHANGE MATERIAL SOLUTIONS AND SHAPE STABLE THERMOSET PHASE CHANGE MATERIAL GELS FORMED THEREFROM

(71) Applicant: MICROTEK LABORATORIES, INC., Dayton, OH (US)

(72) Inventor: Richard M. Formato, Grafton, MA (US)

(73) Assignee: MICROTEK LABORATORIES, INC., Dayton, OH (US)

( * ) Notice: Subject to any disclaimer, the term of this patent is extended or adjusted under 35 U.S.C. 154(b) by 886 days.

(21) Appl. No.: 17/187,033

(22) Filed: Feb. 26, 2021

(65) Prior Publication Data

US 2021/0269582 A1    Sep. 2, 2021

Related U.S. Application Data

(60) Provisional application No. 62/983,391, filed on Feb. 28, 2020.

(51) Int. Cl.
C09K 5/06 (2006.01)
A61F 7/02 (2006.01)
(Continued)

(52) U.S. Cl.
CPC ............ C08G 18/8175 (2013.01); A61F 7/02 (2013.01); C08G 18/69 (2013.01); C08K 5/01 (2013.01);
(Continued)

(58) Field of Classification Search
CPC .......... C09K 5/06; C09K 5/063; C09K 5/066; F25D 3/02; F25D 3/04; F25D 3/045;
(Continued)

(56) References Cited

U.S. PATENT DOCUMENTS 6,841,116 B2 *   1/2005   Schmidt ................. B33Y 10/00
                                                                  425/375
6,865,906 B1     3/2005   Sabin
(Continued)

FOREIGN PATENT DOCUMENTS

WO   WO-2019014215 A1 *   1/2019   ............. C09K 5/063
WO   WO-2019068458 A1 *   4/2019   ............. C09K 5/063
WO   WO-2020077555 A1 *   4/2020

OTHER PUBLICATIONS

Mao et al., A 3D Printable Thermal Energy Storage Crystalline Gel Using Mask-Projection Stereolithography, Polymers, 2018, pp. 1-14, 10, 1117, MDPI.
(Continued)

*Primary Examiner* — Matthew R Diaz
(74) *Attorney, Agent, or Firm* — FisherBroyles, LLP; Susan M. Oiler

(57) ABSTRACT

Radiation curable phase change solutions (PCM) and said solutions as a thermoset thermal energy gels (a radiation cured polymeric network) has a hydrophobic PCM, a polybutadiene urethane acrylate oligomer soluble in the hydrophobic PCM and present as 7% wt/wt to 25% wt/wt of the gel, a photoinitiator soluble in the hydrophobic PCM and present as 0.01% wt/wt to 0.5% wt/wt of the gel, a monofunctional or di-functional crosslinker soluble in the hydrophobic PCM and present as 0% wt/wt to 10% wt/wt of the gel, and a hydrogenated styrenic block copolymer as a secondary resin as 0% to 20% wt/wt of the gel and optionally a tertiary resin as 0% to 5% wt/wt of the gel, wherein the tertiary resin is a hydrogenated styrenic block copolymer that is different than the secondary resin. The solution or gel is sealed in a container, e.g., a sachet, to form a cold pack.

29 Claims, 12 Drawing Sheets

(51) Int. Cl.
*C08G 18/69* (2006.01)
*C08G 18/81* (2006.01)
*C08K 5/01* (2006.01)
*C08K 5/3412* (2006.01)
*C08K 5/5397* (2006.01)
*C08L 53/02* (2006.01)

(52) U.S. Cl.
CPC .......... *C08K 5/3412* (2013.01); *C08K 5/5397* (2013.01); *C09K 5/063* (2013.01); *A61F 2007/0219* (2013.01); *A61F 2007/0292* (2013.01); *C08G 2220/00* (2013.01); *C08L 53/025* (2013.01)

(58) Field of Classification Search
CPC ...... F25D 3/06; F25D 3/08; A61F 7/02; A61F 2006/0219; A61F 2007/0257; A61F 2007/0292; C08G 18/69; C08G 18/8175; C08G 2220/00; C08K 5/01; C08K 5/3412; C08K 5/5397; C08L 53/02; C08L 53/025
See application file for complete search history.

(56) References Cited

U.S. PATENT DOCUMENTS

| | | | |
|---|---|---|---|
| 7,378,460 B2 | 5/2008 | Schmidt et al. | |
| 7,399,796 B2 | 7/2008 | Xu et al. | |
| 7,994,256 B2 | 8/2011 | St. Clair | |
| 8,309,621 B2 | 11/2012 | Breton et al. | |
| 8,916,084 B2 | 12/2014 | Chretien et al. | |
| 9,556,373 B2 * | 1/2017 | Formato | C09K 5/06 |
| 9,598,622 B2 * | 3/2017 | Formato | C08K 5/01 |
| 10,308,827 B2 | 6/2019 | Chopra et al. | |
| 2005/0215724 A1 | 9/2005 | St. Clair | |
| 2005/0215725 A1 | 9/2005 | St. Clair | |
| 2017/0174956 A1 * | 6/2017 | Ramon-Gimenez | C09J 5/06 |
| 2019/0217553 A1 | 7/2019 | Horwath | |

OTHER PUBLICATIONS

Kraton TM Polymers for Oil Modification: Versatile Solutions for Synthetic and Natural Based Oils, 2016, (pp. 8).
Oktay et al., Designing Coconut Oil Encapsulated Poly(stearyl methacrylate-co-hydroxyethyl metacrylate) Based Mictocapsule for Phase Change Materials, ChemistrySelect, 2019, pp. 5110-5115, 4, Wiley-VCH Verlag GmbH & Co.
Yu et al., Graphene-Modified Hydrate Salt/UV-Curable Resin Form-Stable Phase Change Materials: Continuously Adjustable Phase Change Temperature and Ultrafast Solar-to-Thermal Conversion, Energy & Fuels, 2019, pp. 7634-7644, 33, American Chemical Society.
Basturk et al. Photocrosslinked Biobased Phase Change Material for Thermal Energy Storage, Journal of Applied Polymer Science, 2016, pp. 8, Wiley Periodicals, Inc.
Luyt et al., Phase Change Materials Formed by UV Curable Epoxy Matrix and Fischer-Tropsh Paraffin Wax, Energy Conversion and Management, 2009, pp. 57-61, 50, Elsevier.
Basturk et al., A Novel UV-Cured Interpenetrating Organic-Inorganic Hybrid Polymer Network Based Phase Change Materials (IPN-PCM), Society of Plastics Engineers, 2017, pp. 870-875, Wiley Online Library.
International Search Report and Written Opinion, WO2021174026, Jul. 8, 2021 (14 pages).
Extended European Search Report, Application No. 21761750.5, Feb. 5, 2024, p. 1-6.
Meracryl Hema 98 (formerly Visiomer Hema 98), Technical Datasheet by Roehm, date unkown; https://www.meracryl.com/en/meracryl-hema-98.

* cited by examiner

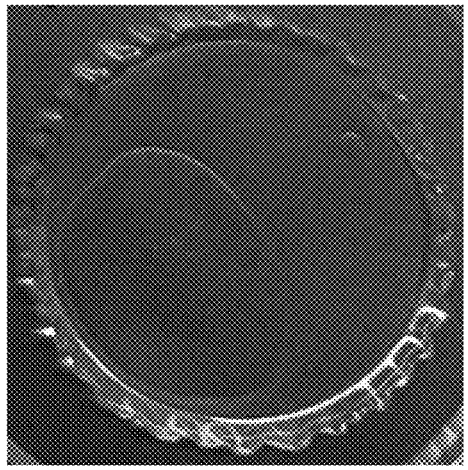
FIG. 4
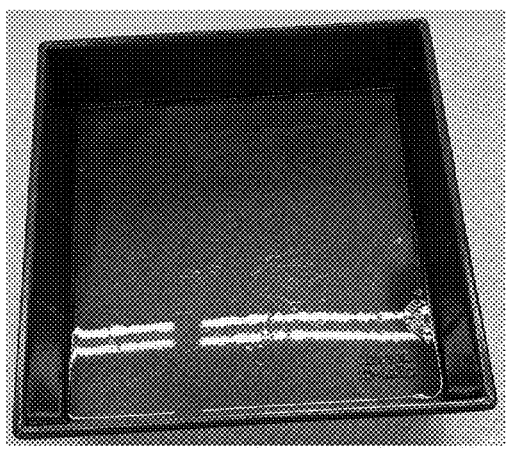 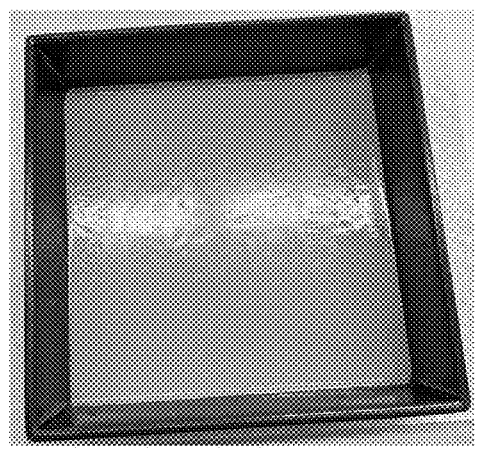
FIG. 5A FIG. 5B

FIG. 17

SUMMARY: Compare Formulations F113 and F120A

HQ Test Results

| ID# (#) | Description Name/ID | DeltaH (melt) (J/g), % of PCM | Tm [C] | Delta H (freeze) (J/g), % of PCM | Tf [C] | Smell Test (HQ) | As Made Sticky? | Color (Yellow) | POST SYN Surface Wet? | POST SYN (%wt loss) |
|---|---|---|---|---|---|---|---|---|---|---|
| PCM6 | Lot# PC06-000602 | 197 | 4.99 | 192 | 0.21 | NA | NA | NO | NA | NA |
| F113 PRE cure | F113 Liquid Pre-Cure | 155 (79%) | 3.46 | 152 (78%) | -2.21 | 4 of 6 (OK) | NA | YES | NA | NA |
| F113P1,2,3 | F113 Pouches (1 sec) | 150 (76%) | 7.49 | 147 (77%) | -5.60 | NT | No | Minor | Relatively Dry | (-0.1%) PASS |
| F120A PRE cure | F110A Liquid Pre-Cure | 154 (78%) | 3.53 | 151 (79%) | -2.23 | 5 of 6 (OK) | NA | NO | NA | NA |
| F120AP1,2,3 | F120A Pouches (1 sec) | 147 (75%) | 5.26 | 143 (74%) | -7.27 | NT | Yes | None | A bit wet | (-0.2%) PASS |

F113 = 1% VAP + 18% 641E (19% wt solids)

F120A = 0% VCA{ + 21% 641E (21% wt solids)

RADIATION CURABLE PHASE CHANGE MATERIAL SOLUTIONS AND SHAPE STABLE THERMOSET PHASE CHANGE MATERIAL GELS FORMED THEREFROM

RELATED APPLICATIONS

This application claims the benefit of U.S. Provisional Application No. 62/983,391, filed Feb. 28, 2021, the entirety of which is incorporated herein by reference.

TECHNICAL FIELD

The present application relates to radiation curable phase change material (PCM) solutions and shape stable thermoset phase change material gels formed therefrom after exposure to radiation, more particularly, to radiation curable phase change material solutions and thermoset thermal energy gels comprising a hydrophobic PCM, a polybutadiene urethane acrylate resin with or without a thickener resin, a mono-functional or di-functional crosslinker, and a photoinitiator, which are all soluble in the hydrophobic PCM.

BACKGROUND

Phase change materials (PCMs) have been utilized as thermal energy storage systems for decades due to their ability to store and release energy in the form of heat during a phase transition, most commonly from the solid to liquid states. PCMs exist in many forms including organic, inorganic, eutectics, and solid-solid. With this wide variety, a range of (phase change) temperatures for different applications can be achieved. It is important to have a PCM phase change temperature in a workable range for the application in order to get the full charge of energy out of (or into) the system. These storage systems can be implemented in many different applications such as bedding, textiles, electronics, bio-tech, and pharmaceutical.

A commonly known application of energy storage is in the form of cold pack therapy. Cold packs are generally water based formulations that once active, keep their surroundings cold for a specified amount of time. They are commonly used as first aid relief, and food and beverage controlled refrigeration. Water is one of the best known PCMs due to its high latent heat value of 334 J/g, but water also has disadvantages. Water melts around 0° C., however, it can be super cooled to temperatures on the order of −40° C. Most commercial freezers only reach temperatures in the −23° C. to −15° C. range, which presents a problem for a water based formulation that requires freeze temperatures lower than that to charge the PCM completely.

While there are commercial products, such as instant ice packs, that base their phase change on the presence of water, its efficacy is often diluted by the other additives needed to improve the formula in other areas, like viscosity, and freeze temperature. Often times these additives dilute the enthalpy available of the water, therefore hindering its efficacy as a PCM.

Other thermal energy storage systems are sol-gel PCM systems, but the lack of high temperature stability of the resulting gel can be an issue, for example, more than ten percent weight of the PCM may be lost at 250° C., as determined by thermogravimetric analysis. Other physical gel based PCMs may be susceptible to flow at temperatures above 35° C., which can render the gelled PCM undesirable for certain packaging applications.

There is a need for new and improved thermal energy storage systems utilizing PCMs that are creep resistant above room temperature, maintain the weight of the PCM at higher temperatures, are easy to manufacture, are adaptable to existing manufacturing methods and machinery, and meet other adopted product specifications.

SUMMARY

A radiation curable phase change material solution has been developed that meets the above identified needs and produces a shape stable PCM gel upon exposure to radiation. Interestingly, skepticism and doubt was encountered upon requesting radiation curable resins from suppliers, so much so that some suppliers would not send samples. In fact the supplier of one of the ultraviolet/electron beam (UV/EB) curable resins that was successful did not want to send samples because the supplier was sure that it would not cure a hydrophobic phase change material, especially considering the large thicknesses desired in use (ideally greater than 1").

In all aspects, radiation curable phase change solutions have a hydrophobic phase change material, a radiation curable polybutadiene urethane acrylate oligomer soluble in the hydrophobic phase change material and present as 7% wt/wt to 25% wt/wt of the solution, a photoinitiator soluble in the hydrophobic phase change material and present as 0.01% wt/wt to 0.5% wt/wt of the solution, and a mono-functional or di-functional crosslinker soluble in the hydrophobic phase change material and present as 0% wt/wt to 10% wt/wt of the solution. Upon exposure to radiation the solution cures to form a thermoset gel.

In all aspects, any or all of the following further define the compositions: the polybutadiene urethane acrylate is a difunctional aliphatic polybutadiene urethane acrylate; the hydrophobic phase change material is selected from the group consisting of an n-alkane, a fatty acid methyl ester, a fatty alcohol, a fatty acid, and mixtures thereof; the n-alkane is saturated and has carbon atoms within the range of $C_{10}$-$C_{40}$; the photoinitiator comprises phosphine oxide; when the crosslinker is a mono-functional crosslinker, the mono-functional crosslinker comprises a mono-functional vinyl caprolactam, a mono-functional lauryl acrylate, a mono-functional isobornyl acrylate, an aliphatic monofunctional acrylate, an ethoxylated nonyl-phenol acrylate, an alkoxylated nonyl-phenol acrylate, or a 4-tert-butyl cyclohexyl acrylate; when the crosslinker is a di-functional crosslinker, the di-functional crosslinker comprises a di-functional 1,6-hexanediol diacrylate, di-functional 3-methyl-1, 5-pentanediol diacrylate, hydroxy pivalic acid neopentyl glycol diacrylate, or 2-butyl-2-ethyl 1,3-propanediol diacrylate; the balance is the hydrophobic phase change material.

In one embodiment, a hydrogenated styrenic block copolymer is present as a secondary resin and is present as 0.5% to 20% wt/wt of the gel. This embodiment can include a tertiary resin as 0.5% to 5% wt/wt of the gel. The tertiary resin is also a hydrogenated styrenic block copolymer, but it is different than the secondary resin. In another embodiment, the tertiary resin is present as 1% to 2% wt/wt of the gel and the secondary resin is present as 1% to 10% wt/wt of the gel. The secondary resin and the tertiary resin are both styrene-ethylene-butylene-styrene linear polymers with tri-block structures.

In all aspects, the cured thermoset gel having the same composition as the radiation curable phase change solution are disclosed. The thermoset gel is shape stable in that it supports its own weight, after 20 freeze/thaw cycles has weight loss of 1% or less, and is creep resistant up to 60° C.

In another aspect, cold packs are disclosed that are a container sealingly enclosing the radiation curable phase change solution or said solution once cured into a thermoset gel. The container can permanently enclose the solution or the gel. The container can be a rigid container that retains a preselected shape and configuration or a flexible container that is conformable to a surface against which the flexible container is seated.

In yet another aspect, methods of making the thermoset thermal energy gel from the radiation curable phase change material solution discussed above include providing a hydrophobic phase change material in its liquid state, adding a mono-functional or di-functional crosslinker and a radiation curable resin thereto while maintaining the liquid state of the hydrophobic phase change material to form a liquid homogenous mixture, adding a photoinitiator to the liquid homogenous mixture with stirring to form a final mixture, the photoinitiator being soluble in the hydrophobic phase change material, and curing the final mixture by exposure to radiation, thereby forming a thermoset thermal energy gel.

Adding the mono-functional or di-functional crosslinker and the radiation curable resin is sequential by either forming a first mixture of the hydrophobic phase change material and the mono-functional or di-functional crosslinker or of the hydrophobic phase change material and the radiation curable resin. The method optionally includes heating the radiation curable resin to a preselected temperature that liquifies or renders the resin flowable. In one embodiment, the radiation curable resin is a polybutadiene urethane acrylate oligomer and the preselected temperature is at most 65° C.

In one embodiment, the first mixture is of the hydrophobic phase change material and the radiation curable resin, and the method comprises cooling the first mixture to room temperature before adding the mono-functional or di-functional crosslinker.

In all aspects, the method includes placing the final mixture in a container and cooling the final mixture to room temperature before curing the final mixture. The radiation is ultra-violet radiation, visible radiation, electron beam radiation or a combination thereof, and the curing takes 1 second to 15 seconds and is applied at a radiation intensity of at least 100 mW/cm$^2$ and a radiation dose of 100 to 200 mJ/cm$^2$. The thermoset gel is shape stable in that it supports its own weight, after 20 freeze/thaw cycles has weight loss of 1% or less, and is creep resistant up to 60° C., and the container can be a rigid or flexible container.

BRIEF DESCRIPTION OF THE DRAWINGS

FIG. 4 is a photograph of a shape stable cured PURE-TEMP® 4 PCM gel.

FIG. 5A is a photograph of a shape stable cured n-hexacosane PCM gel at a temperature at which the PCM is in the liquid state.

FIG. 5B is a photograph of a shape stable cured n-hexacosane PCM gel at a temperature at which the PCM is in the solid (frozen) state.

FIG. 17 is a chart reporting tested properties for two selected trials from FIGS. 13-15 that had the most suitable properties.

DETAILED DESCRIPTION

The following detailed description will illustrate the general principles of the invention, examples of which are additionally illustrated in the working and comparative examples.

As used herein, "gel" means a coherent mass consisting of a liquid in which particles too small to be seen in an ordinary optical microscope are either dispersed or arranged in a fine network throughout the mass. A gel may be notably elastic and jellylike (as gelatin or fruit jelly), or quite solid and rigid (as silica gel, a material that looks like coarse white sand and is used as a dehumidifier). Gels are colloids (aggregates of fine particles, as described above, dispersed in a continuous medium) in which the liquid medium is immobilized in the fine network by surface tension effects.

As used herein "soluble" means that a substance can be dissolved in another, typically called the solvent, by physical rather than chemical means. In this application, the hydrophobic phase change material is the solvent and the dissolution preferably occurs at ambient or room temperature. Room temperature is typically 25° C., but can vary by +/−5° C. When the two substances being mixed are both in the liquid phase, the liquids are "miscible" if the solute is soluble at all proportions in the hydrophobic phase change material.

As used herein "shape stable" means a gel that supports its own weight, does not leak PCM at room temperature, retains its shape upon exposure to 60° C. for 1 hour, and after 20 freeze/thaw cycles has minimal liquid PCM weight loss (e.g., ideally less than 1.5% or less than 1%).

Radiation curing equipment is generally divided into two types: Broad Spectrum and Light Emitting Diode (LED). Both of these are further comprised of flood cure and conveyor cure options. Radiation utilized can be ultra-violet (UV) radiation, visible (VIS) radiation or electron beam (EB) radiation. The UV spectrum is typically broken down into three ranges, specifically UVA (315 to 400 nm), UVB (280 to 315 nm) and UVC (100 to 280 nm). LEDs can use both UV (100 to 400 nm) and Visible (400 to 700 nm) radiation to effect cure, and typically have the majority of their intensity centered around a specific wavelength (e.g., 365 nm, 385 nm, 405 nm). Shorter wavelengths are used to promote surface cure, while longer wavelengths are used to promote depth of cure. For example, some commercially available bulbs focus energy in the shortwave, longwave and visible regions. For the purposes of making the thermoset thermal energy gel, both standard mercury arc UV bulbs and LED bulbs were used to cure PCM material solutions in both flood cure and conveyor cure setups, without any obvious change in gel properties.

Figure 1:
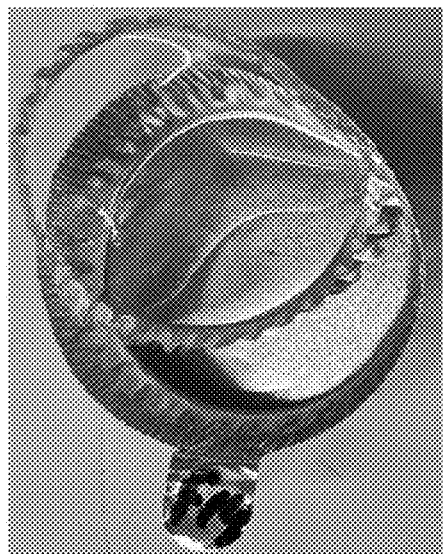
FIG. 1 is a photograph of a shape stable cured n-tetradecane PCM gel.
Figure 2:
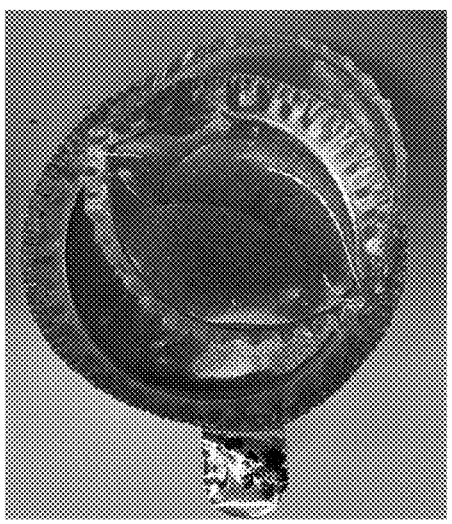
FIG. 2 is a photograph of a shape stable cured n-hexadecane PCM gel.
Figure 3A:
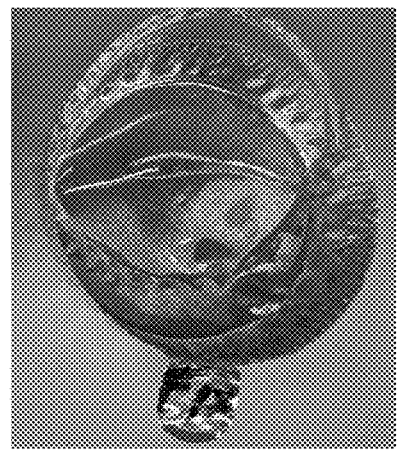
FIG. 3A is a photograph of a shape stable cured n-octadecane PCM gel at a temperature at which the PCM is in the liquid state.
Figure 3B:
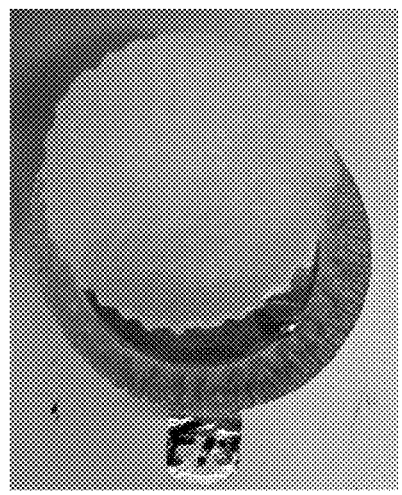
FIG. 3B is a photograph of a shape stable cured n-octadecane PCM gel at a temperature at which the PCM is in the solid (frozen) state.
Figure 6:
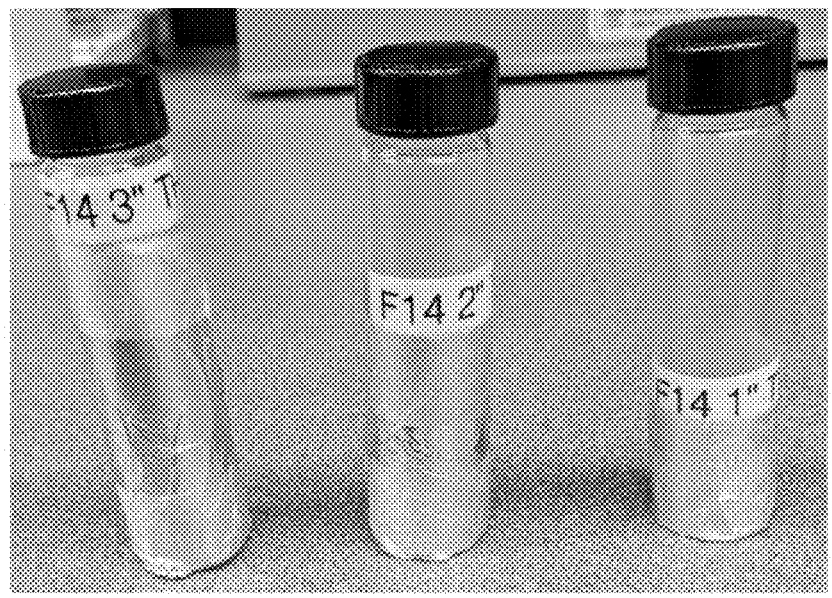
FIG. 6 is a photograph of radiation curable PCM solutions in vials having different heights, i.e., one inch, two inches, and three inches to test curing effectiveness, covered with foil so that curing occurred from the top downward.
Figure 7:
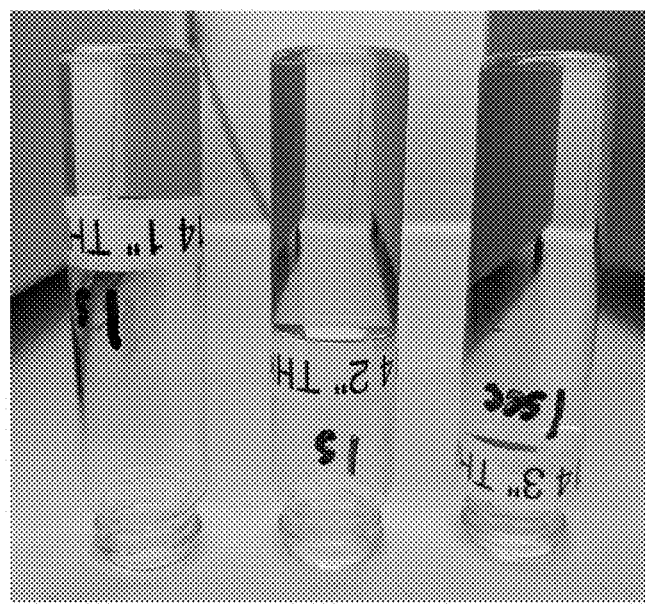
FIG. 7 is a photograph of the three vials of FIG. 6 after exposure to UV radiation for one second with the foil removed.
Figure 8:
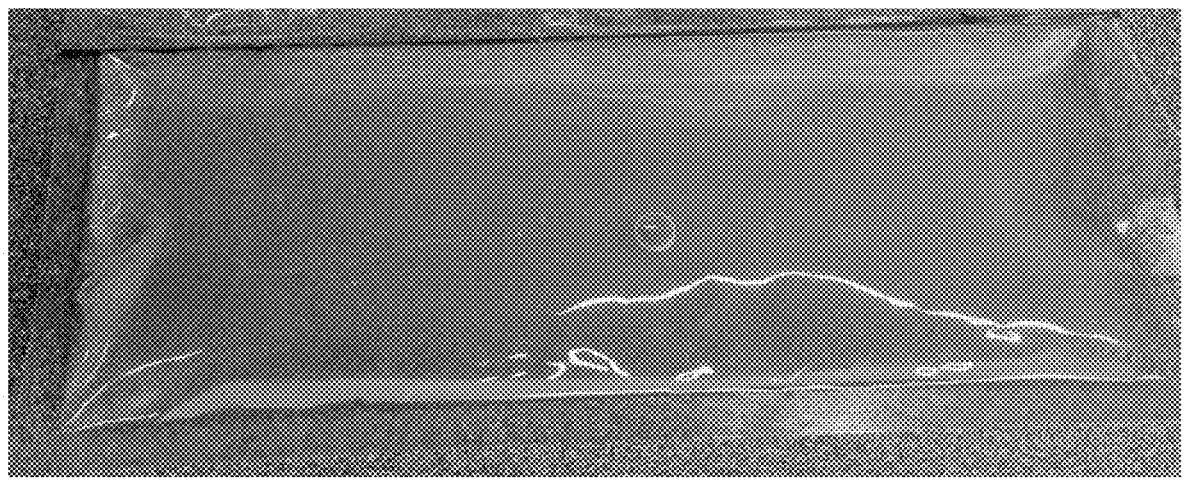
FIG. 8 is a photograph of a sachet of 8 in×3 in×0.5 in, sealed and containing 120 grams of a radiation curable PCM formulation.

A radiation curable phase change material solution has been developed that produces a shape stable, thermoset PCM gel upon exposure to radiation, which solves the problems with existing PCM gels and meets the needs of the industry. The exposure time to radiation is in a range of 1 second to 15 seconds (e.g., intensity of 170 mW/cm$^2$ with corresponding dose of 170 mJ/cm$^2$ to 2550 mJ/cm$^2$), more preferably 1 second to 8 seconds (e.g., dose up to 1360 mJ/cm$^2$). In one embodiment, as shown in FIGS. 6 and 7, up to 3 inches of the solution cured in just 1 second. No matter what format or curing equipment was utilized, flood cure or conveyor cure, a minimum surface intensity of 100 mW/cm$^2$ for a duration between 1 to 2 seconds (dose of 100 to 200 mJ/cm$^2$) was found to cure the phase change material solution.

The radiation curable phase change solution has a hydrophobic phase change material, a radiation curable polybutadiene urethane acrylate oligomer soluble in the hydrophobic phase change material and present as 7% wt/wt to 25% wt/wt of the gel, a photoinitiator soluble in the hydrophobic phase change material and present as 0.01% wt/wt to 0.5% wt/wt of the gel, and a mono-functional or di-functional crosslinker soluble in the hydrophobic phase change material and present as 0.1% wt/wt to 10% wt/wt of the gel. The balance of the gel is the hydrophobic phase change material.

The radiation curable phase change solution contains between 10% to 30% solids, preferably 13% to 25% solids, more preferably 13% to 20% solids, typically with less than 20% solids.

Phase Change Material

The phase change material is a heat-absorbing material that has a melting point at about -30° C. to about 150° C., more preferably -30° C. to about 80° C., and is hydrophobic. The PCM can be selected from straight chain alkanes, alcohols, organic acids, and aliphatic acids containing at least 6 carbon atoms, and mixtures thereof. More specifically, suitable hydrophobic materials include, but are not limited to, aliphatic hydrocarbyl compounds such as saturated or unsaturated $C_{10}$-$C_{40}$ hydrocarbons, which are branched or preferably linear; cyclic hydrocarbons; aromatic hydrocarbyl compounds; $C_1$-$C_{40}$-alkyl-substituted aromatic hydrocarbons; saturated or unsaturated $C_6$-$C_{30}$-fatty acids; fatty alcohols; C-esters; and natural and synthetic waxes.

Examples of aliphatic hydrocarbyl compounds such as saturated or unsaturated $C_{10}$-$C_{40}$ hydrocarbons, which are branched or preferably linear, include, but are not limited to n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, and n-octacosane, some of which are listed in the table below with their melting points. These PCMs are sometimes called paraffinic hydrocarbons and their melting point is directly related to the number of carbon atoms.

TABLE 1

| Compound Name | Carbon Atoms | Melting Point (° C.) |
|---|---|---|
| n-Octacosane | 28 | 61.4 |
| n-Heptacosane | 27 | 59.0 |
| n-Hexacosane | 26 | 56.4 |
| n-Pentacosane | 25 | 53.7 |
| n-Tetracosane | 24 | 50.9 |
| n-Tricosane | 23 | 47.6 |
| n-Docosane | 22 | 44.4 |
| n-Heneicosane | 21 | 40.5 |
| n-Eicosane | 20 | 36.8 |
| n-Nonadecane | 19 | 32.1 |
| n-Octadecane | 18 | 28.2 |
| n-Heptadecane | 17 | 22.0 |
| n-Hexadecane | 16 | 18.2 |
| n-Pentadecane | 15 | 10.0 |
| n-Tetradecane | 14 | 5.9 |
| n-Tridecane | 13 | -5.5 |

Examples of cyclic hydrocarbons include, but are not limited to, cyclohexane, cyclooctane, and cyclodecane. Examples of aromatic hydrocarbyl compounds include, but are not limited to, benzene, naphthalene, biphenyl, o- or n-terphenyl. Examples of $C_1$-$C_{40}$-alkyl-substituted aromatic hydrocarbons include, but are not limited to, dodecylbenzene, tetradecylbenzene, hexadecylbenzene, hexylnaphthalene or decyinaphthalene. Examples of saturated or unsaturated $C_6$-$C_{30}$-fatty acids include, but are not limited to, lauric, stearic, oleic, linoleic, caprylic, capric, myristic, palmitic, behenic acid, and eutectic mixtures thereof, including mixtures with other PCMs described herein. Examples of fatty alcohols include, but are not limited to, lauryl, stearyl, oleyl, myristyl, caprylic, capric, and cetyl alcohols, mixtures such as coconut fatty alcohol, and the so-called oxo alcohols which are obtained by hydroformylation of α-olefins and further reactions. Examples of C-esters include, but are not limited to, $C_1$-$C_{10}$-alkyl esters of fatty acids, such as methyl laurate, methyl myristate, propyl palmitate, methyl stearate or methyl palmitate, and their eutectic mixtures or methyl cinnamate. Examples of natural and synthetic waxes include, but are not limited to, montan acid waxes, montan ester waxes, polyethylene wax, oxidized waxes, polyvinyl ether wax, and ethylene vinyl acetate wax.

Blends of two or more PCMs are often utilized to achieve a specific melting point by taking advantage of eutectic mixture principles. An example of commercially available PCMs are sold under the brand name PURETEMP® from PureTemp, LLC.

Resin

Resins that are likely to be soluble in a hydrophobic PCM include, but are not limited to, rubber elastomers, including silicone rubber (PDMS), polybutadiene, polyisoprene, polyisobutylene, butyl rubber, EPDM, styrene butadiene rubbers, and styrene ethylene rubbers. However, it is unlikely styrene isoprene styrene (SIS), styrene butadiene styrene (SBS) and styrene ethylene butylene styrene (SEBS) will dissolve in n-alkane PCMs at room temperature (approximately 25° C.), requiring the application of heat. A radiation curable polybutadiene urethane acrylate oligomer that is soluble in a hydrophobic PCM is successful in making the shape stable, thermoset gel.

More specifically, a di-functional aliphatic polybutadiene urethane acrylate oligomer (PBDUA) having a viscosity greater than 25,000 cP at 60 C, which is present as 4% wt/wt to 25% wt/wt of the gel, preferably 7% wt/wt to 20% wt/wt, and more preferably 7% wt/wt to 18% wt/wt produces a shape stable thermoset gel in the formulations disclosed herein. Such oligomers are available under the brand name BOMARR from Dymax Corporation. Each of the BOMARR polybutadiene urethane acrylate (PBDUA) oligomers resulted in a cured gel, but it was not obvious that given their polarity, they would dissolve in the hydrophobic PCM. The PBDUA with the highest viscosity provided the best syneresis results after 20 or more freeze/thaw cycles.

The PBDUA, however, is an expensive material. As such, it is desirable to keep the amount of PBDUA used in the formulation in the lower part of the % wt/wt ranges. Take for one non-limiting example, the upper limit of 18% wt/wt PBDUA, this percentage could be subdivided into two or three parts and the second and/or third parts could be replaced/substituted with one or more of the other resins that are soluble in a hydrophobic PCM. A secondary "thickener" resin can be present as 0 to 20% wt/wt of the formulation, more preferably 1% to 10% wt/wt and a tertiary "associate" resin can be present as 0 to 5% wt/wt of the formulation, more preferably 1% to 2% wt/wt. In one embodiment, the 18% wt/wt was split as 8% wt/wt PBDUA and 10% secondary resin. In another embodiment, the 18% wt/wt was split as 8% wt/wt PBDUA and 9% secondary "thickener" resin and 1% tertiary "associate" resin or 8% secondary "thickener" resin and 2% tertiary "associate" resin. In another example, with a total of 14.5% wt/wt to 15.5% wt/wt of the resins, the tertiary resin is in a range of 1% wt/wt to 2% wt/wt and the PBDUA to secondary resin is present at a ratio in a range of 1:1 to 2:1, or 1:1 to 1.9:1, or 1.07 to 1.5:1.

The secondary "thickener" resin and the tertiary "associate" resin comprise hydrogenated styrenic block copolymers (SBCs). Without being bound by theory, it is hypothesized that the secondary and tertiary resins form an interpenetrating network with the PBDUA resin. Example SBCs are available under the KRATON™ brand from Kraton Corporation, including styrene-ethylene-propylene (SEP) polymers, styrene-ethylene-butylene-styrene (SEBS) polymers, and enhanced rubber segments (ERS). Through extensive testing it was determined that the secondary "thickener" resin is either an SEBS/linear polymer with a tri-block structure, a SEBS/linear polymer with a mid-block structure, a SEP polymer with a di-block structure, or a SEBS/ERS/linear polymer that has greater than 10% styrene to less than 45% styrene in a ratio to rubber in a range of 1:1.4 to 6.7, more preferably 1:1.4 to 4, and even more preferably 1:1.4 to 2.3. Further, the secondary resin has a melt flow index of less than 15 g/10 min at 230° C. for 5 kg, or more preferably a melt flow index of less than 6 g/10 min at 230° C. for 5 kg (see Table 2). It was determined that the tertiary "associate" resin is either an SEBS/linear polymer with a triblock structure or a SEP polymer with a di-block structure that has greater than 25% styrene to less than 45% styrene in a ratio to rubber in a range of 1:1.4 to 2.6. Further, the tertiary resin has a melt flow index of less than 5 g/10 min at 230° C. for 5 kg, and more preferably less than 3 g/10 min at 230° C. for 5 kg (see Table 3).

TABLE 2

Secondary Resins

| KRATON™ Name | Polymer/ type | Diblock (%) | Styrene/ Rubber Ratio | Melt Index (g/10 min/ 230° C./ 5 kg) | Brookfield Viscosity 10% w\| 25% w |
|---|---|---|---|---|---|
| G1652 | SEBS/linear/ tri-block | <1 | 30/70 | 5 | 30\|1800 |
| A1536 | SEBS/linear/ mid-block | — | 42/58 | 3 | —\|— |
| G1701 | SEP/di-block | 100 | 37/63 | <1 | —\|>50000 |
| G1645 | SEBS/ERS | 7 | 13/87 | 3 | —\|— |
| G1730 | SEBS/linear | <1 | 20/80 | 11 | 35\|1980 |

TABLE 3

Tertiary Resin

| KRATON™ Name | Polymer/ type | Diblock (%) | Styrene/ Rubber Ratio | Melt Index (g/10 min/ 230° C./ 5 kg) | Brookfield Viscosity (cps) 10% w\| 25% w |
|---|---|---|---|---|---|
| G1651 | SEBS/linear/ tri-block | <1 | 30/70 | <1 | 1800\|>50000 |
| A1536 | SEBS/linear/ mid-block | — | 42/58 | 3 | —\|— |
| G1660 | SEBS/linear | — | 31/69 | <1 | 50\|8000 |
| G1702 | SEP/di-block | 100 | 28/72 | < | 280\|50000 |

KRATON™ FG1924 G polymer is a clear, linear triblock copolymer based on styrene and ethylene/butylene with a polystyrene content of 13%, styrene/rubber ration of 13/87 and a melt index of 40 g/10 min at 230° C. for 5 kg. When this resin was used, the formulations were not able to UV cure. Other resins tested that did not produce suitable gels include KRATON™ MD1646 V linear SEBS triblock copolymer, MD6953 SE Triblock (Star) copolymer with a styrene to rubber ratio of 6/94.

Crosslinker

The crosslinker is a mono-functional or di-functional crosslinker soluble in the hydrophobic phase change material that is present as 0.1% wt/wt to 10% wt/wt of the resulting gel. A mono-functional caprolactone is soluble in the hydrophobic phase change material. The mono-functional caprolactone can be a liquid at room temperature. In one embodiment, V-CAP® vinyl caprolactam (commercially available from Ashland) was utilized. Surprisingly, V-CAP® vinyl caprolactam was suitable for use with the PCM while V-PYROL™/RC reactive monomer (also commercially available from Ashland) was not. Other suitable mono-functional crosslinkers include, but are not limited to, isobornyl acrylate (IBOA) and lauryl acrylate (available under the PHOTOMER™ brand), aliphatic monofunctional acrylate available under the EBECRYL® 113 brand from Allnex Netherlands B.V., ethoxylated nonyl-phenol acrylate and alkoxylated nonyl-phenol acrylates available as SARTOMER® SR504 and SARTOMER® SR614A, respectively, from Sartomer Americas, and 4-tert-butyl cyclohexyl acrylate available under the brand ETERMER® EM105 from Eternal Material Co. Ltd. Example di-functional crosslinkers include, but are not limited to, 1,6-hexanediol diacrylate (HDDA) and 3-methyl-1,5-pentanediol diacrylate (available under the PHOTOMER™ brand), hydroxy pivalic acid neopentyl glycol diacrylate available under the MIRAMER® M210 brand from Miwon Specialty Chemical Co. Ltd., and 2-butyl-2-ethyl 1,3-propanediol diacrylate available under the brand ETERMER® EM229 from Eternal Material Co. Ltd. When comparing gels of the same composition made with di-functional versus mono-functional crosslinkers, mono-functional crosslinkers are beneficial because of their capability to retain shape stability without making the cured gel too brittle.

Photoinitiator

The photoinitiator is one that is soluble in the hydrophobic phase change material and is present as 0.01% wt/wt to 0.5% wt/wt of the gel. A Norrish Type I photoinitiator is preferred, such as a phosphine oxide. The photoinitiator can be a phenyl bis(2,4,6-trimethyl benzoyl)-phosphine oxide, a 2,4,6-trimethylbenzoyl-diphenyl phosphine oxide, a 1-hydroxycyclohexyl-phenyl ketone, a blend of benzophenone and 1-hydroxycyclohexyl-phenyl ketone, a 2-hydroxy-2-methyl-1-phenylpropanone, a blend of 2,4,6-trimethylbenzoyl-diphenyl phosphine oxide and 2-hydroxy-2-methylpropiophenone, bis-acylphosphine oxide (BPO), and ethyl(2,4,6-trimethylbenzoyl)-phenyl phosphinate. Some commercially available examples include, but are not limited to, photoinitiators available under the brand name OMNIRAD® from IGM resins and Speedcure BPO from Sartomer.

The shape stable, thermoset PCM gel has a polymeric network formed by the resin and the cross-linker. The PCM can be considered as macroencapsulated by the polymeric network. In the case where secondary and/or tertiary resins are used, the gel is also characterized by having a physical gel point within the range of room temperature to 50° C. and being conformable, shock absorbing, cuttable, creep resistant at temperatures up to 60° C., and still generally flexible when frozen. Further, in its liquid state, the gel is clear/translucent and completely homogenous. Also, in its liquid state, i.e., before being cured, the gel solution has a viscosity that is pumpable through a sachet machine for filling pouches therewith. In one embodiment, the viscosity of the gel solution is less than 5000 cps at 60° C. In another embodiment, the viscosity of the gel solution is less than 1000 cps at 60° C., and more preferably less than 500 cps at 60° C.

The solid gel can be UV-cured (or cut) into beads or any other pre-selected shape, which can then be inserted into a pliable or rigid container for a variety of end applications. But, more advantageously, the liquid radiation curable PCM solution can be introduced into a pliable or rigid container of a preselected shape and cured directly therein. In most embodiments, the container is selected to be transmissive of radiation. However, the liquid radiation curable PCM solution can be cured from an open end of a container, if the container is not transmissive of radiation. In one example embodiment, the gels can be housed in a container to form a cold pack, typically permanently enclosing the thermal gel therein. The container can be a rigid container that retains a preselected shape and configuration, or a flexible container that is conformable to a surface against which the flexible container is seated. A rigid container may be made of glass, metal, hard-plastic, styrofoam containers, or other suitable materials. A flexible container may be made of polymer films, plastics (such as a plastic in the form of a bag or sachet), watertight fabrics, or other suitable materials.

Methods for making thermoset thermal energy gel and the solution from which the gel is formed are disclosed herein. The methods include mixing a hydrophobic phase change material and a mono-functional or di-functional crosslinker, which is soluble in the hydrophobic phase change material, at ambient temperature to form a first mixture. In a separate vessel, if needed, the radiation curable resin is heated to at most 65° C., more preferred at most 60° C., to allow ease of handling when the resin has a high viscosity, without allowing onset of thermal curing. The radiation curable resin is one that is soluble in the hydrophobic phase change material. Next, the heated radiation curable resin is added, with mixing, to the first mixture to form a second mixture. A photoinitiator is added to the second mixture with stirring to form a final mixture, which may or may not be slightly heated (e.g., up to 40 C) to ensure complete dissolution of the photoinitiator. The photoinitiator is also soluble in the hydrophobic phase change material. The final mixture is cooled to ambient temperature and placed in one or more selected containers, which may be rigid or flexible as described above.

Alternatively, the heated radiation curable resin can be added to the hydrophobic phase change material, with mixing until dissolution to make a first mixture, followed by the addition of the crosslinker with mixing until dissolution to make the second mixture. This would be followed by the addition of the photoinitiator (with or without heating, as needed) to make the final mixture. The cooling and placing in containers may occur in any order. Lastly, the final mixture is cured by exposure to radiation, thereby forming a thermoset thermal energy gel.

The photoinitiator is added last and can be added at any time after formulation of the second mixture, even as much as four weeks later, i.e., the second mixture is shelf stable at room temperature without the photoinitiator. This shelf stability is very useful in manufacturing. In another embodiment, the photoinitiator may be added while the second mixture is maintained at a temperature of 40° C. with mixing for 30 minutes to 2 hours, depending on heating apparatus and its configuration. Heating the second mixture above 40° C. may be required depending on the melt temperature of the hydrophobic phase change material.

In one embodiment, the containers in which the final mixture will be cured is a sachet or lager plastic bags that can be fluidly sealed to contain the final mixture permanently therein. Sachet and bag filling machines, which are readily available, are used to manufacture liquid filled pouches of phase change materials. As such, the final mixture can be cured in-situ after a preselected amount is placed in the container and exposed to radiation. The container may be placed in radiation flood cure equipment and/or proceed through a conveyor equipped with radiation cure capability. The radiation may be ultra-violet (UV) radiation, visible (VIS) radiation and/or electron beam (EB) radiation. A minimum surface intensity of 100 mW/cm$^2$ for a duration between 1 to 2 seconds (dose of 100 to 200 mJ/cm$^2$) was found to cure the phase change material solutions described herein, but the times will vary relative to the intensity of the radiation, and the particular composition of the formulation.

Working Example 1

A radiation curable phase change solution was formulated according to Table 4 by mixing the n-tetradecane and the vinyl caprolactam, which is soluble in the n-tetradecane, at ambient temperature to form a first mixture. In a separate vessel, the di-functional aliphatic polybutadiene urethane acrylate oligomer was heated to 65° C., and thereafter was added, with mixing, to the first mixture to form a second mixture. The phenyl bis(2,4,6-trimethyl benzoyl)-phosphine oxide was added to the second mixture with stirring to form a final mixture. The final mixture was cooled to ambient temperature and was poured in to one or more containers and exposed to radiation to cure the solution into a gel.

TABLE 4

| Name | Function | Trial 1 % wt/wt |
|---|---|---|
| phenyl bis (2,4,6-trimethyl benzoyl)-phosphine oxide | Photoinitiator | 0.06% |
| vinyl caprolactam | Crosslinker | 7% |
| di-functional aliphatic poly-butadiene urethane acrylate oligomer | UV/EB Resin | 16% |
| n-tetradecane | Phase change material | 76.94% |

The PCM solution in Table 4 was reproduced using n-hexadecane and n-octadecane in place of n-tetradecane, which are considered to be Trial 2 and Trial 3. Shape stable cured thermoset gels resulted for each n-alkane phase change material.

Creep testing was conducted by heating the gels at 25° C. for 1 hour and then increasing the temperature by 5° C. for each subsequent hour through the temperature of 60° C. Gels that evidenced no creep are desirable. Creep is the tendency of a solid material to move slowly or slowly deform over a long period of exposure to high levels of stress, here, increasing temperature. The gel of Table 4 and its duplications with n-hexadecane and n-octadecane each evidence no creep.

Working Example 2

Additional samples were made using the same method, but the amount of the vinyl caprolactam were reduced. The inventive examples in Table 5 produced gels that were shape stable. However, gels that did not have any vinyl caprolactam produced "marginally" shape stable gels. While keeping the sum of the crosslinker and oligomer constant, the best overall combination of retaining shape stability while minimizing syneresis were using small amounts (e.g., up to 1% wt) of vinyl caprolactam with the balance being PBDUA oligomer.

TABLE 5

| Name | Trial 4 % wt/wt | Trial 5 % wt/wt | Trial 6 % wt/wt | Trial 7 % wt/wt | Trial 8 % wt/wt |
|---|---|---|---|---|---|
| phenyl bis (2,4,6-trimethyl benzoyl)-phosphine oxide | 0.06% | 0.06% | 0.06% | 0.06% | 0.06% |
| vinyl caprolactam | 5.36% | 3.67% | 1.94% | 1.81% | 1.46% |
| di-functional aliphatic polybutadiene urethane acrylate oligomer | 16.41% | 16.71% | 11.01% | 17.03% | 17.10% |
| n-tetradecane | 78.23% | 79.62% | 87.05% | 81.16% | 81.46% |

Samples were made using the same method, but the amount of the radiation curable resin was reduced. The inventive Examples in Table 6 below produced gels that were shape stable. It was determined that samples with less than 8% of the radiation curable resin were not shape stable.

TABLE 6

| Name | Trial 9 % wt/wt | Trial 10 % wt/wt | Trial 11 % wt/wt |
|---|---|---|---|
| phenyl bis (2,4,6-trimethyl benzoyl)-phosphine oxide | 0.06% | 0.06% | 0.06% |
| vinyl caprolactam | 7.21% | 7.45% | 7.59% |
| di-functional aliphatic polybutadiene urethane acrylate oligomer | 13.73% | 10.39% | 8.83% |
| n-tetradecane | 79.43% | 82.15% | 83.68% |

Working Example 3

In a Trial 12, the n-tetradecane from Example 1 was replaced with PURETEMP® 4 PCM from PureTemp LLC, a fatty acid methyl ester type PCM. The method of making Trial 12 was identical to that in Working Example 1. The thermoset UV cured gel was both shape stable and showed no creep when exposed to temperatures up to 60° C.

Working Example 4

In Trail 13, the n-tetradecane from Example 1 was replaced with n-hexacosane. The thermoset UV cured gel was shape stable and showed no creep when exposed to temperatures up to 70° C. The method of making the cure gel was modified, from the procedure given above, to accommodate the PCM being frozen below its phase change temperature of approximately 57° C. The modified method was as follows: The n-hexacosane was liquified by heating to 70° C., followed by addition of the PBDUA oligomer, which was heated to 65° C., with mixing. Once the first mixture was homogeneous, vinyl caprolactam was added, with mixing while maintaining the temperature at 65° C., until the second mixture was homogenous. The second mixture was stored at 65° C. until it was ready for addition of photoinitiator. When gels were to be made, the photoinitiator was added, with mixing at 65° C., until the final mixture was obtained. The final mixture was kept at 65° C., in a heated oven which was shielded from UV/visible light. Samples were made by pouring the heated final mixture into a (heated) mold of the desired shape, and exposed to radiation while ensuring the n-hexacosane remained in its liquid state. Once the thermoset gel had been radiation cured, it was immediately cooled to very low temperatures (−80° C.) so that the frozen radiation cured thermoset shape stable gel could be ejected from the mold. The sample, still frozen, was allowed to return to room temperature where it was ready for further evaluation.

In addition to creep testing, syneresis testing was conducted on the samples. Syneresis testing was based on completing at least 20 freeze and thaw cycles. Samples that weighed the same or lost 1% or less in weight were considered acceptable. Only Trial 11 had a syneresis that was greater than 1% weight loss.

Working Example 5

Table 7 below includes a plurality of example formulations based on the formulation from Table 4. Here, four different phase change materials from various categories were used to demonstrate that each produced a successful solution and each produced a shape stable cured gel.

TABLE 7

| Phase Change Material 77% wt/wt | UV/EB Resin 16% wt/wt | Crosslinking Agent 7% wt/wt | Photoinitiator 0.06% wt/wt |
|---|---|---|---|
| methyl palmitate | di-functional aliphatic polybutadiene urethane acrylate oligomer | vinyl caprolactam | phenyl bis (2,4,6-trimethyl benzoyl)-phosphine oxide |
| methyl myristate | di-functional aliphatic polybutadiene urethane acrylate oligomer | vinyl caprolactam | phenyl bis (2,4,6-trimethyl benzoyl)-phosphine oxide |
| dodecanol | di-functional aliphatic polybutadiene urethane acrylate oligomer | vinyl caprolactam | phenyl bis (2,4,6-trimethyl benzoyl)-phosphine oxide |
| decanol | di-functional aliphatic polybutadiene urethane acrylate oligomer | vinyl caprolactam | phenyl bis (2,4,6-trimethyl benzoyl)-phosphine oxide |

Caprylic acid was tried in the same formulation, but did produce a successful gel. A shape stable gel did occur with a change of photoinitiator and crosslinking agent as set forth in Table 8 below. The crosslinking agent was changed from a mono-functional crosslinking agent to a di-functional crosslinking agent, but the weight percentages were maintained.

TABLE 8

| Phase Change Material 77% wt/wt | UV/EB Resin 16% wt/wt | Crosslinking Agent 7% wt/wt | Photoinitiator 0.06% wt/wt |
|---|---|---|---|
| caprylic acid | di-functional aliphatic polybutadiene urethane acrylate oligomer | 2-butyl-2-ethyl 1,3-propanediol diacrylate | bis acyl phosphine oxide |
| caprylic acid | di-functional aliphatic polybutadiene urethane acrylate oligomer | hydroxy pivalic acid neopentyl glycol diacrylate | bis acyl phosphine oxide |

Working Example 6

Figure 13:
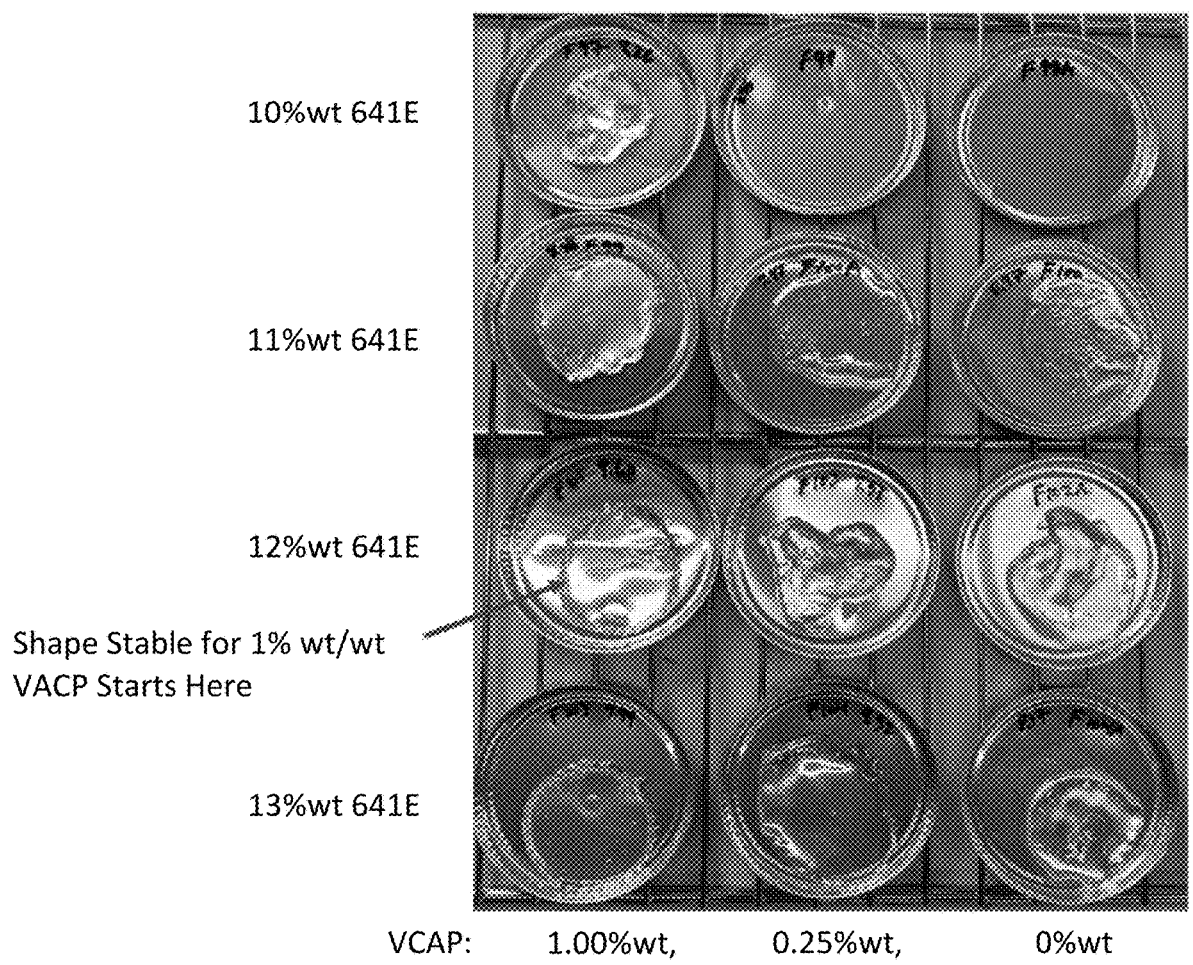
FIG. 13 is a photograph in chart-style showing cured gels at increasing weight percentages of UV/EB resin for three different weight percentages of crosslinking agent.
Figure 14:
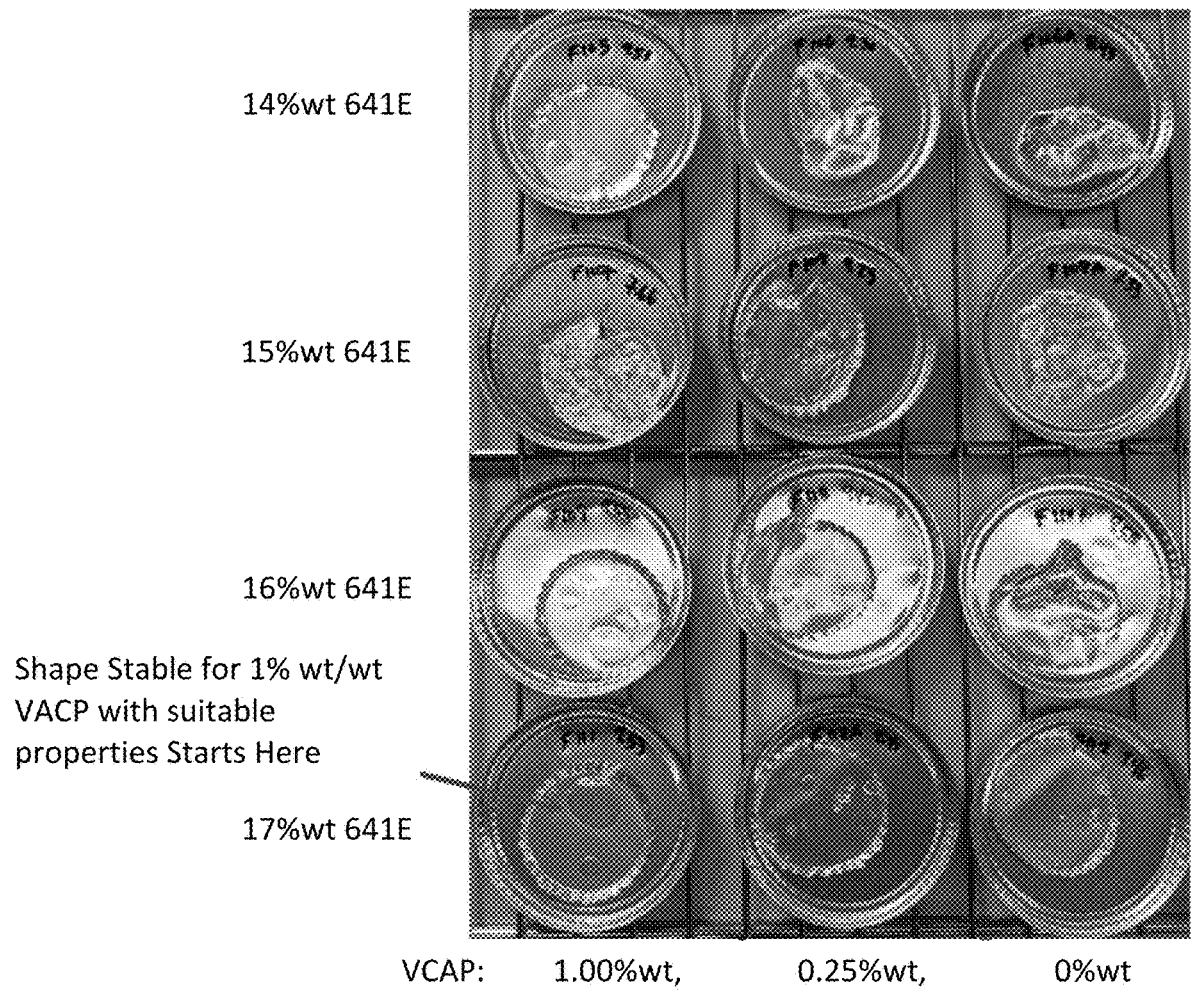
FIG. 14 is a photograph in chart-style that is a continuation of FIG. 13.
Figure 15:
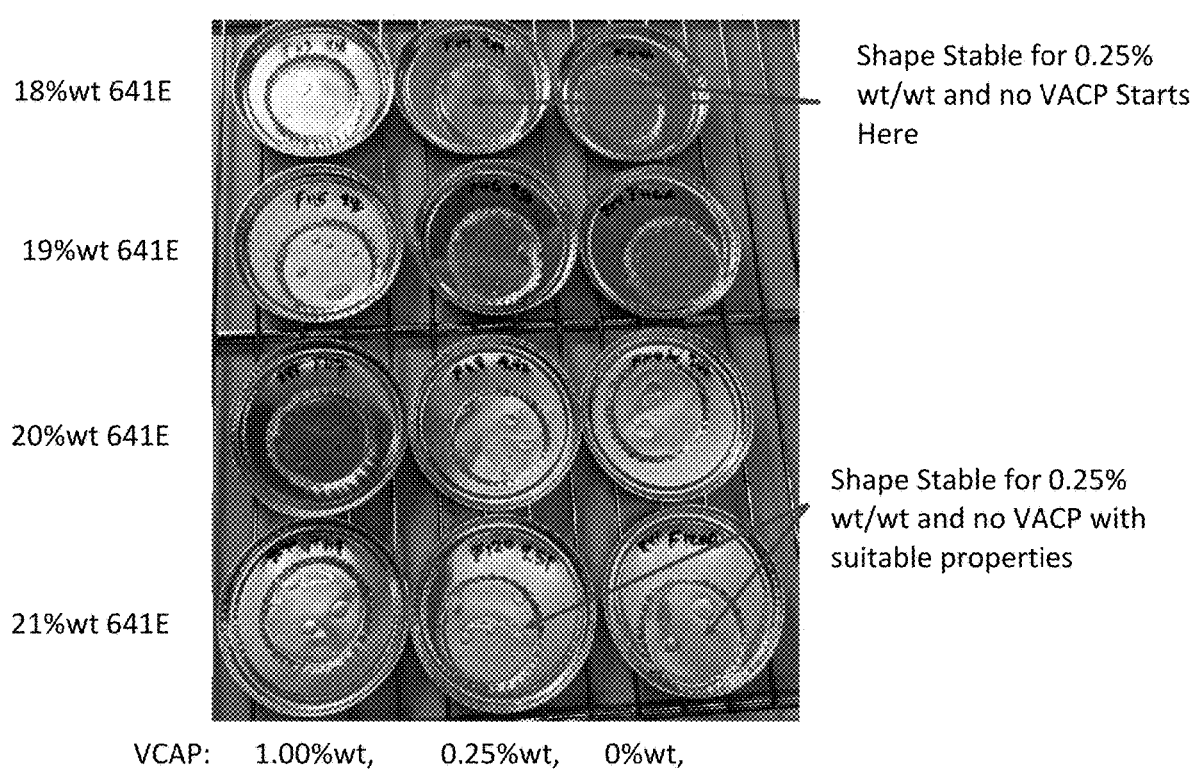
FIG. 15 is a photograph in chart-style that is a continuation of FIG. 14.
Figure 16:
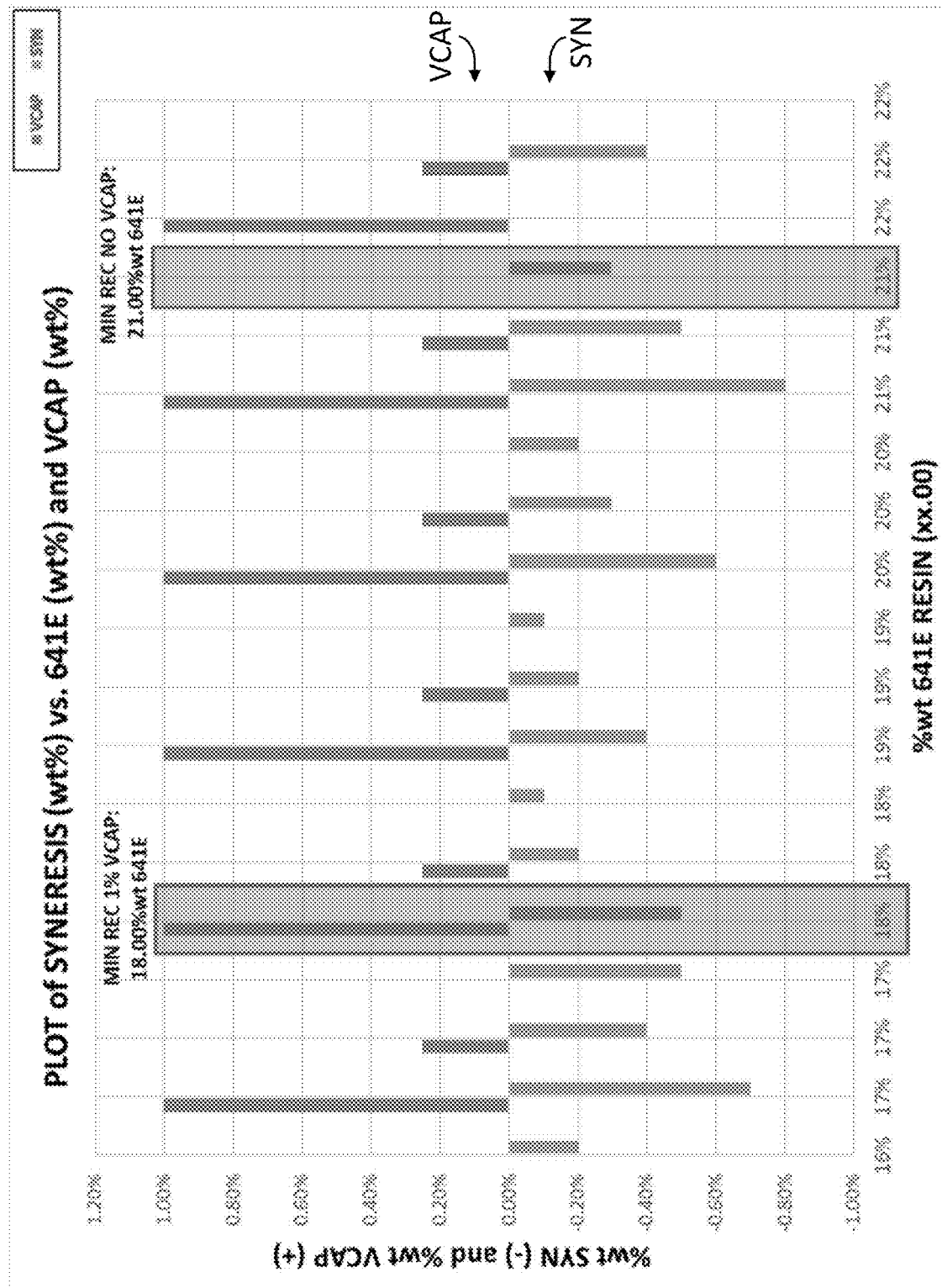
FIG. 16 is a bar graph of syneresis data for the samples shown in FIGS. 13-15.

Tests were conducted based on the formulation in Table 4 above to determine the % wt/wt of the UV/EB Resin needed relative to using 1% or less wt/wt of the crosslinker. The % wt/wt of the crosslinker was selected as 1% wt/wt, 0.25% wt/wt, and 0% wt/wt and the UV/EB Resin was tested over the range of 10% wt/wt to 21% wt/wt in 1% increments. Photographs of the cured gels over these ranges are includes as FIGS. 13-15. Here, when the % wt/wt of the crosslinker was decreased the amount of the PCM was added in its place, which reduces the % solids present in the formulations. Each solution in this Working Example has about 23% wt/wt solids content. The data in FIGS. 13-17 demonstrates that the cured gels that were made with 1% wt/wt VCAP crosslinking agent showed shape stability beginning at 12% wt/wt UV/EB resin and had suitable properties at 17% wt/wt to 18% wt/wt UV/EB resin. The data demonstrates that the cured gels that were made with 0.25% wt/wt or 0% wt/wt VCAP crosslinking agent showed shape stability beginning at 18% wt/wt UV/EB resin and had suitable properties at 21% wt/wt UV/EB resin. The suitable properties included syneresis, post-cure enthalpy, smell, stickiness, and wetness.

Working Example 7

The most expensive component in each formulation above is the UV/EB resin, di-functional aliphatic polybutadiene urethane acrylate oligomer. So, determining a formulation using a smaller amount of the UV/EB resin that still produces a UV curable gel that is shape stable and has a suitable viscosity pre-cure that is pumpable for filling pouches, e.g., pumpable through a sachet filling machine is no easy task. Through numerous experimental trials a plurality of polymer thickeners for hydrophobic substances based on styrene-ethylene polymers, such as styrene-ethylene-butylene styrene polymers (SEBS), styrene-ethylene-propylene (SEP), and styrene-ethylene-propylene-styrene (SEPS) were evaluated for inclusion in the formulations as a means to reduce the amount of the UV/EB resin present.

It was experimentally determined that the combination of KRATON™ G1652 SEBS polymer with a tri-block structure as the secondary resin and KRATON™ G1651 SEBS polymer with a tri-block structure as the tertiary resin produced a successful UV curable formulation having 16.5% solids according to the formulations in Table 9.

TABLE 9

| | UV/EB Resin | PCM | Crosslinker | Secondary Resin | Tertiary Resin | photoinitiator |
|---|---|---|---|---|---|---|
| Trial 14 | 7.5% PBDUA | 83.5% PCM6 | 1% VCAP | 7% G1652 SEBS | 1% G1651 SEBS | 0.06% BPO |
| Trial 15 | 7.5% PBDUA | 83.5% PCM6 | 1% VCAP | 6% G1652 SEBS | 2% G1651 SEBS | 0.06% BPO |

For the formulations in Table 9, 10 grams of solution was made by mixing and all but the photoinitiator in an oven set at 70° C. until the ample was homogenized. The solution was not allowed to reach 70° C. The samples were left to cool at room temperature. Prior to UV curing, the photoinitiator was added with mixing after warming the previously cooled sample in an oven set at 70° C. The samples were placed in an aluminum weigh pan and irradiated with UV light (about 170 mW/cm$^2$) at a distance therefrom of 5 inches.

Next, each sample was placed in a thermal chamber for syneresis analysis, exposure to 20+ freeze/thaw cycles with a cycle being approximately 17 degrees above and below the phase change temperature. Syneresis data is reported as % loss of the mass of the sample.

The formulations in Table 9 were tried with no VCAP as well. When the VCAP was omitted, the % wt/wt was added in the form of additional PCM to maintain the % solids.

When no VCAP was present, the formulations did not produce successful UV cured gels that are shape stable after syneresis testing.

Working Example 8

Using the Trial 14 formulation in Table 9 as a basis for further testing, the Tertiary Resin was replaced with KRATON™ A1536 SEBS polymer with a mid-block structure, KRATON™ G1660 SEBS linear polymer with a tri-block structure, and KRATON™ G1702 SEP polymer with a di-block structure, respectively, as set forth in Tables 10-12, below in combination with various Secondary Resins.

Post-UV cure, each sample was removed from the aluminum weigh pan, weighed, imaged and observed for gel properties. Next, each sample was placed in a thermal chamber for syneresis analysis, as described in working example 7. Syneresis data is reported as % loss of the mass of the sample.

TABLE 10

Tertiary Resin is KRATON™ G1160 SEBS polymer

| UV/EB Resin 7.5% | PCM 83.5% | Crosslinker 1% | Secondary Resin 7% | Tertiary Resin 1% | photoinitiator 0.06% | % loss |
|---|---|---|---|---|---|---|
| PBDUA | PCM6 | VCAP | KRATONTM G1701 | G1660 SEBS | BPO | 0.75 |
| PBDUA | PCM6 | VCAP | KRATONTM G1645 | G1660 SEBS | BPO | 0.77 |
| PBDUA | PCM6 | VCAP | KRATONTM G1652 | G1660 SEBS | BPO | 0.90 |
| PBDUA | PCM6 | VCAP | KRATONTM G1657 | G1660 SEBS | BPO | 1.59 |
| PBDUA | PCM6 | VCAP | KRATONTM G1702 | G1660 SEBS | BPO | Not shape stable |
| PBDUA | PCM6 | VCAP | KRATONTM G1730 | G1660 SEBS | BPO | 0.53 |
| PBDUA | PCM6 | VCAP | KRATONTM G1750 | G1660 SEBS | BPO | Not shape stable |
| PBDUA | PCM6 | VCAP | KRATONTM MD1646 | G1660 SEBS | BPO | 1.11 |
| PBDUA | PCM6 | VCAP | KRATONTM MD6953 | G1660 SEBS | BPO | Not shape stable |
| PBDUA | PCM6 | VCAP | KRATONTM A1536 | G1660 SEBS | BPO | 0.81 |

TABLE 11

Tertiary Resin is KRATON™ A1536 SEBS polymer

| UV/EB Resin 7.5% | PCM 83.5% | Crosslinker 1% | Secondary Resin 7% | Tertiary Resin 1% | photoinitiator 0.06% | % loss |
|---|---|---|---|---|---|---|
| PBDUA | PCM6 | VCAP | KRATONTM G1701 | A1536 SEBS | BPO | 0.73 |
| PBDUA | PCM6 | VCAP | KRATONTM G1645 | A1536 SEBS | BPO | 1.07 |
| PBDUA | PCM6 | VCAP | KRATONTM G1652 | A1536 SEBS | BPO | 0.97 |
| PBDUA | PCM6 | VCAP | KRATONTM G1657 | A1536 SEBS | BPO | 2.34 |
| PBDUA | PCM6 | VCAP | KRATONTM G1702 | A1536 SEBS | BPO | 2.09 |
| PBDUA | PCM6 | VCAP | KRATONTM G1730 | A1536 SEBS | BPO | 0.81 |
| PBDUA | PCM6 | VCAP | KRATONTM G1750 | A1536 SEBS | BPO | Not shape stable |
| PBDUA | PCM6 | VCAP | KRATONTM MD1646 | A1536 SEBS | BPO | 3.15 |
| PBDUA | PCM6 | VCAP | KRATONTM MD6953 | A1536 SEBS | BPO | Not shape stable |

TABLE 12

Tertiary Resin is KRATON™ G1702 SEBS polymer

| UV/EB Resin 7.5% | PCM 83.5% | Crosslinker 1% | Secondary Resin 7% | Tertiary Resin 1% | photoinitiator 0.06% | % loss |
|---|---|---|---|---|---|---|
| PBDUA | PCM6 | VCAP | KRATONTM G1701 | G1702 SEBS | BPO | 0.92 |
| PBDUA | PCM6 | VCAP | KRATONTM G1645 | G1702 SEBS | BPO | Not shape stable |
| PBDUA | PCM6 | VCAP | KRATONTM G1652 | G1702 SEBS | BPO | 1.18 |
| PBDUA | PCM6 | VCAP | KRATONTM G1657 | G1702 SEBS | BPO | Not shape stable |
| PBDUA | PCM6 | VCAP | KRATONTM G1730 | G1702 SEBS | BPO | Not shape stable |
| PBDUA | PCM6 | VCAP | KRATONTM G1750 | G1702 SEBS | BPO | Not shape stable |
| PBDUA | PCM6 | VCAP | KRATONTM MD1646 | G1702 SEBS | BPO | Not shape stable |
| PBDUA | PCM6 | VCAP | KRATONTM MD6953 | G1702 SEBS | BPO | Not shape stable |
| PBDUA | PCM6 | VCAP | KRATONTM A1536 | G1702 SEBS | BPO | 0.92 |

With respect to Tables 10-12, the syneresis (% loss) data was evaluated as follows: (i) if the % loss was 1% or less, then the formulation was considered "green"—a useful formulation; (ii) if the % loss was in the range of 1.5% or less to 1%, then the formulation was considered "yellow"—a reasonably useful formulation; and (iii) if the % loss was greater than 1.5%, then the formulation was considered "red"—a non-viable formulation. All formulations that were labeled as "not shape stable" are non-viable formulations as well. These samples could not be reweighed after the completion of syneresis testing.

Moreover, it is always desirable to have the greatest possible amount of the PCM present for maximum thermal control in the end product. Increasing the amount of the PCM while decreasing the amount of the resin will decrease the percent solids in the formulation.

Advantages

Figure 9:
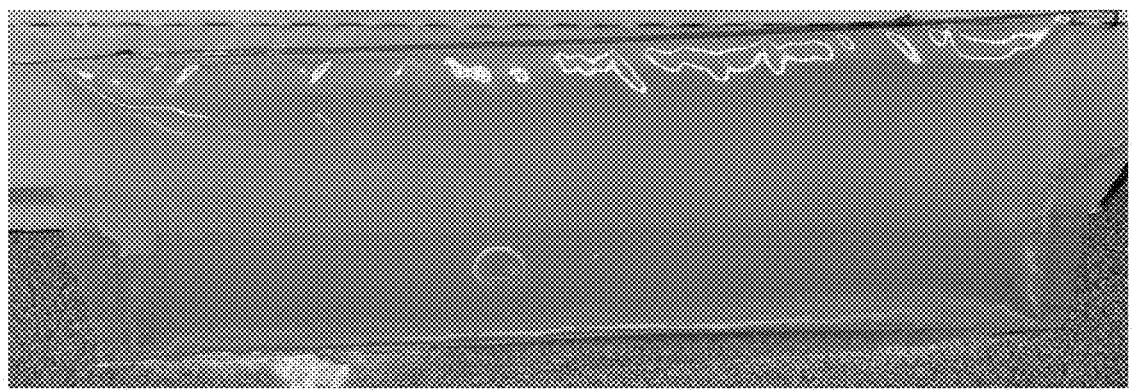
FIG. 9 is a photograph of the sachet of FIG. 6 containing the cured PCM gel, standing vertically, after exposure to UV radiation for 7 seconds.
Figure 10:
FIG. 10 is a photograph of a sachet of 8 in×5 in×0.5 in containing 240 grams of cured PCM gel, standing vertically, after exposure to UV radiation for 1 second.
Figure 11:
FIG. 11 is a photograph of an amber bottle within a cup surrounded by a cured thermoset thermal energy gel.
Figure 12:
FIG. 12 is a photograph of an amber bottle within a Styrofoam housing with a cured thermoset thermal energy gel cured within the cavity surrounding the bottle.

The thermoset thermal energy gel has numerous advantages including that it is shape stable in whatever geometry, even complex 3-D geometries, is desired, see FIGS. 7, 9 and 10 for a few non-limiting examples. Further, being shape stable, the composition will not leak if the packaging is punctured. The gel in-place-nature of the radiation curable PCM solution improves coverage/contact between the product to be protected. The gel provides mechanical protection to the product, such as drop, shock, and vibration protection, because of the elastomeric nature of the gel and the gel is soft and conformable (i.e., not rigid). The PCM solution cures quickly, is workable at room temperature, and can be cured in-situ. It is even possible to cure the PCM solution by 3D printing.

With respect to manufacturing, the PCM solution being stable at room temperature makes it easy to handle and the solution can replace existing liquid PCMs in existing manufacturing lines as long as the package, container, or housing receiving the PCM solution is radiation transparent, such that the PCM solution can be cured while therein. For example, the PCM solution can replace a liquid PCM that is filled into sachets in a sachet filling machine. The manufacturer would only need to add a UV flood cure and/or a UV conveyor system at the end of the existing manufacturing line.

Having described the invention in detail and by reference to specific embodiments and examples, it will be apparent that numerous modifications and variations are possible without departing from the spirit of the invention as defined by the following claims.

What is claimed is:

1. A thermoset thermal energy gel comprising:
  a radiation cured polymeric network formed from
    a hydrophobic phase change material;
    a polybutadiene urethane acrylate oligomer soluble in the hydrophobic phase change material and present as 7% wt/wt to 25% wt/wt of the thermoset thermal energy gel;
    a photoinitiator soluble in the hydrophobic phase change material and present as 0.01% wt/wt to 0.5% wt/wt of the thermoset thermal energy gel; and
    a mono-functional crosslinker soluble in the hydrophobic phase change material, present as 0.1% wt/wt to 10% wt/wt of the thermoset thermal energy gel and selected from the group consisting of a mono-functional vinyl caprolactam, an aliphatic monofunctional acrylate, an ethoxylated nonyl-phenol acrylate, an alkoxylated nonyl-phenol acrylate, a 4-tert-butyl cyclohexyl acrylate, and combinations thereof.

2. The thermoset thermal energy gel of claim 1, wherein the thermoset thermal energy gel is shape stable in that it supports its own weight and after 20 freeze/thaw cycles has weight loss of 1% or less.

3. The thermoset thermal energy gel of claim 2, wherein the thermoset thermal energy gel is creep resistant up to 60° C.

4. The thermoset thermal energy gel of claim 1, wherein the polybutadiene urethane acrylate oligomer is a difunctional aliphatic polybutadiene urethane acrylate oligomer.

5. The thermoset thermal energy gel of claim 1, wherein the hydrophobic phase change material is selected from the group consisting of an n-alkane, a fatty acid methyl ester, a fatty alcohol, a fatty acid, and mixtures thereof.

6. The thermoset thermal energy gel of claim 5, wherein the n-alkane is saturated and has an amount of carbon atoms within the range of $C_{10}$-$C_{40}$.

7. The thermoset thermal energy gel of claim 1, wherein the photoinitiator comprises phosphine oxide.

8. The thermoset thermal energy gel of claim 1, wherein when the mono-functional crosslinker is present as 0.1% wt/wt to 1% wt/wt of the thermoset thermal energy gel, the polybutadiene urethane acrylate oligomer is present as 18% wt/wt to 21% wt/wt of the thermoset thermal energy gel.

9. The thermoset thermal energy gel of claim 1, wherein a balance is the hydrophobic phase change material is present in an amount of a balance of the thermoset thermal energy gel.

10. The thermoset thermal energy gel of claim 1, further comprising a hydrogenated styrenic block copolymer as a secondary resin as 0.5% to 20% wt/wt of the thermoset thermal energy gel.

11. The thermoset thermal energy gel of claim 10, further comprising a tertiary resin as 0.5% to 5% wt/wt of the thermoset thermal energy gel, wherein the tertiary resin is a hydrogenated styrenic block copolymer that is different than the secondary resin.

12. The thermoset thermal energy gel of claim 11, wherein the tertiary resin is present as 1% to 2% wt/wt of the thermoset thermal energy gel and the secondary resin is present as 1% to 10% wt/wt of the thermoset thermal energy gel.

13. The thermoset thermal energy gel of claim 12, wherein the secondary resin and the tertiary resin are both styrene-ethylene-butylene-styrene linear polymers with tri-block structures.

14. A radiation curable phase change solution comprising:
a hydrophobic phase change material;
a radiation curable polybutadiene urethane acrylate oligomer soluble in the hydrophobic phase change material and present as 7% wt/wt to 25% wt/wt of the radiation curable phase change solution;
a photoinitiator soluble in the hydrophobic phase change material and present as 0.01% wt/wt to 0.5% wt/wt of the radiation curable phase change solution; and
a mono-functional or di-functional crosslinker soluble in the hydrophobic phase change material and present as 0.1% wt/wt to 10% wt/wt of the radiation curable phase change solution;
wherein upon exposure to radiation the radiation curable phase change solution cures to form a thermoset gel;
wherein the radiation curable phase change solution comprises less than 30% solids and has a viscosity less than 5000 cP at 60° C.

15. The radiation curable phase change solution of claim 14, wherein the polybutadiene urethane acrylate oligomer is a difunctional aliphatic polybutadiene urethane acrylate oligomer.

16. The radiation curable phase change solution of claim 14, wherein the hydrophobic phase change material is selected from the group consisting of an n-alkane, a fatty acid methyl ester, a fatty alcohol, a fatty acid, and mixtures thereof.

17. The radiation curable phase change solution of claim 16, wherein the n-alkane is saturated and has an amount of carbon atoms within the range of $C_{10}$-$C_{40}$.

18. The radiation curable phase change solution of claim 14, wherein the photoinitiator comprises phosphine oxide.

19. The radiation curable phase change solution of claim 14, wherein the crosslinker is a mono-functional crosslinker, and the mono-functional crosslinker comprises a mono-functional vinyl caprolactam, a mono-functional lauryl acrylate, a mono-functional isobornyl acrylate, an aliphatic monofunctional acrylate, an ethoxylated nonyl-phenol acrylate, an alkoxylated nonyl-phenol acrylate, or a 4-tert-butyl cyclohexyl acrylate.

20. The radiation curable phase change solution of claim 14, wherein the crosslinker is a di-functional crosslinker, and the di-functional crosslinker comprises a di-functional 1,6-hexanediol diacrylate, di-functional 3-methyl-1,5-pentanediol diacrylate, hydroxy pivalic acid neopentyl glycol diacrylate, or 2-butyl-2-ethyl 1,3-propanediol diacrylate.

21. The radiation curable phase change solution of claim 14, wherein the hydrophobic phase change material is present in an amount of a balance of the radiation curable phase change solution.

22. The radiation curable phase change solution of claim 14, further comprising a hydrogenated styrenic block copolymer as a secondary resin as 0.5% to 20% wt/wt of the radiation curable phase change solution.

23. The radiation curable phase change solution of claim 22, further comprising a tertiary resin as 0.5% to 5% wt/wt of the radiation curable phase change solution, wherein the tertiary resin is a hydrogenated styrenic block copolymer that is different than the secondary resin.

24. The radiation curable phase change solution of claim 23, wherein the tertiary resin is present as 1% to 2% wt/wt of the radiation curable phase change solution and the secondary resin is present as 1% to 10% wt/wt of the radiation curable phase change solution.

25. The radiation curable phase change solution of claim 24, wherein the secondary resin and the tertiary resin are both styrene-ethylene-butylene-styrene linear polymers with tri-block structures.

26. A cold pack comprising:
a container sealingly enclosing the thermoset thermal energy gel of claim 1.

27. The cold pack of claim 26, wherein the container permanently encloses the thermoset thermal energy gel.

28. The cold pack of claim 26, wherein the container is a rigid container that retains a preselected shape and configuration.

29. The cold pack of claim 26, wherein the container is a flexible container that is conformable to the surface against which the flexible container is seated.

* * * * *